United States Patent

Walter

(12) United States Patent
(10) Patent No.: US 6,262,058 B1
(45) Date of Patent: Jul. 17, 2001

(54) PYRIMIDIN-4-ONE DERIVATIVES AS PESTICIDE

(75) Inventor: Harald Walter, Rodersdorf (CH)

(73) Assignee: Syngenta Crop Protection, Inc., Greensboro, NC (US)

(*) Notice: Subject to any disclaimer, the term of this patent is extended or adjusted under 35 U.S.C. 154(b) by 19 days.

(21) Appl. No.: 09/125,760

(22) PCT Filed: Mar. 3, 1997

(86) PCT No.: PCT/EP97/01056

§ 371 Date: Aug. 25, 1998

§ 102(e) Date: Aug. 25, 1998

(87) PCT Pub. No.: WO97/33890

PCT Pub. Date: Sep. 18, 1997

(30) Foreign Application Priority Data

Mar. 11, 1996 (CH) .................................... 635/96

(51) Int. Cl.$^7$ .................... A01N 43/54; C07D 495/04
(52) U.S. Cl. ............................. 514/258; 544/278
(58) Field of Search ..................... 544/278; 514/258

(56) References Cited

U.S. PATENT DOCUMENTS

| | | | |
|---|---|---|---|
| 3,674,786 | 7/1972 | Rajappa | 544/255 |
| 4,442,289 | 4/1984 | Kienzle | 544/280 |
| 6,066,638 | * 5/2000 | Bereznak et al. | 514/258 |

FOREIGN PATENT DOCUMENTS

| | | |
|---|---|---|
| 313284 | 2/1974 | (AU) . |
| 313285 | 2/1974 | (AU) . |
| 1 950 990 | 5/1970 | (DE) . |
| 24 11 273 | 9/1975 | (DE) . |
| 240892 | 11/1986 | (DE) . |
| 0 043 054 | 1/1982 | (EP) . |
| 0 276 825 | 8/1988 | (EP) . |
| 0 733 633 | 9/1996 | (EP) . |
| 94/26722 | 11/1994 | (WO) . |
| 97022562 | * 1/1997 | (WO) . |

OTHER PUBLICATIONS

Blaskiewics, P., et al., Chem. Abstr., vol. 83, No. 206324f, p. 402 (1975).

Boehm, R, et al., Chem. Abstr., vol. 107, No. 77829n, p. 709 (1987). *

Devani, et al., Chem. Abstr., vol. 85, No. 46566x, p. 529 (1976). *

Devani, M.B., et al., "Synthesis of 3–Substituted Thieno [2,3–d]pryimidin–4(3H)–one–2–mercaptoacetic Acids and Their Ethyl Esters for Pharmacological Screening," J. of Pharm. Sciences, vol. 65, No. 5, pp. 660–664 (1976).

Indian J. Chemistry Sect. B, vol. 30B, No. 6, pp. 618–619 (1991).

Khim, Geterotsikl, Soedin. vol. 3, pp. 413–418 (1988). *

Khripak, S.M., et al., Chem. Abstr., vol. 111, No. 232726e, p.782n (1989). *

Pathak, U.S., et al., Chem. Abstr., vol. 115, No. 183226p, p. 919–920 (1991). *

Sauter, F, et al., "N–[BIS(Methylthio)Methylene]Amino Esters (BMMA): Novel Reagents for Annelation of Pyrimidine Moieties," Heterocycles, vol. 40, No. 2, pp. 851–865 (1995). *

Tanaka, K., et al., "Synthesis and Reaction of 5–Amino–3–trifluoromethylisoxazole and –Pyrazole–4–carboxylic Acids," J. Heterocyclic Chem., vol. 23, pp. 1535–1538 (1986). *

* cited by examiner

*Primary Examiner*—Richard L. Raymond
(74) *Attorney, Agent, or Firm*—William A. Teoli, Jr.

(57) ABSTRACT

The present invention relates to novel pyrimidin-4-one derivatives of formula I, which have pesticidal activity, in particular fungicidal activity,

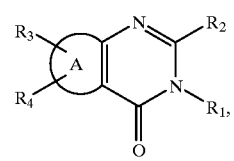

I wherein
$R_1 = C_1-C_6$alkyl, $C_2-C_6$alkenyl, $C_2-C_6$alkynyl, $C_3-C_6$cycloalkyl, each of which is unsubstituted or substituted by halogen;
$R_2 = OR_5$;
$R_3$ and $R_4$ are each independently of the other hydrogen, halogen;
$R_5$ is $C_1-C_6$alkyl or $C_3-C_6$cycloalkyl each unsubstituted or halogen-substituted; and
A=thienyl.

3 Claims, No Drawings

PYRIMIDIN-4-ONE DERIVATIVES AS PESTICIDE

This application is a 371 of PCT/EP97/01056, filed Mar. 3, 1997.

The present invention relates to novel pyrimidin-4-one derivatives of formula I, which have pesticidal activity, in particular fungicidal activity,

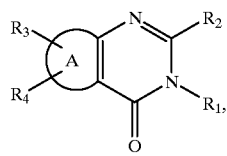

wherein
$R_1=C_1-C_6$alkyl, $C_2-C_6$alkenyl, $C_2-C_6$alkynyl, $C_3-C_6$cycloalkyl, each of which is unsubstituted or substituted by halogen;
$R_2=OR_5$;
$R_3$ and $R_4$ are each independently of the other hydrogen, halogen;
$R_5$ is $C_1-C_6$alkyl or $C_3-C_6$cycloalkyl each unsubstituted or halogen-substituted; and
A=thienyl.

The invention also relates to the preparation of these compounds, to agrochemical compositions comprising as active ingredient at least one of these compounds, as well as to the use of the active ingredients or compositions for pest control, in particular as fungicides, in agriculture and horticulture.

The compounds I and, optionally, their tautomers may be obtained in the form of their salts. Because the compounds I have at least one basic centre they can, for example, form acid addition salts. Said acid addition salts are, for example, formed with mineral acids, typically sulfuric acid, a phosphoric acid or a hydrogen halide, with organic carboxylic acids, typically acetic acid, oxalic acid, malonic acid, maleic acid, fumaric acid or phthalic acid, with hydroxycarboxylic acids, typically ascorbic acid, lactic acid, malic acid, tartaric acid or citric acid, or with benzoic acid, or with organic sulfonic acids, typically methane acid or p-toluenesulfonic acid.

Together with at least one acidic group, the compounds of formula I can also form salts with bases. Suitable salts with bases are, for example, metal salts, typically alkali metal salts or alkaline earth metal salts, e.g. sodium salts, potassium salts or magnesiumsalts, or salts with ammonia or an organic amine, e.g. morpholine, piperidine, pyrrolidine, a mono-, di- or trialkylamine, typically ethylamine, diethylamine, triethylamine or dimethylpropylamine, or a mono-, di- or trihydroxyalkylamine, typically mono-, di- or triethanolamine. Where appropriate, the formation of corresponding internal salts is also possible. Within the scope of this invention, agrochemically acceptable salts are preferred.

Where asymmetrical carbon atoms are present in the compounds of formula I, these compounds are in optically active form. Owing to the presence of double bonds, the compounds can be obtained in the [E] and/or [Z] form. Atropisomerism can also occur. The invention relates to the pure isomers, such as enantiomers and diastereomers, as well as to all possible mixtures of isomers, e.g. mixtures of diastereomers, racemates or mixtures of racemates.

The general terms used hereinabove and hereinbelow have the following meanings, unless otherwise defined:

Alkyl groups are, in accordance with the number of carbon atoms, straight-chain or branched and will typically be methyl, ethyl, n-propyl, isopropyl, n-butyl, sec-butyl, isobutyl, tert-butyl, n-amyl, tert-amyl, 1-hexyl or 3-hexyl.

Alkenyl will be understood as meaning straight-chain or branched alkenyl such as allyl, methallyl, 1-methylvinyl or but-2-en-1-yl. Preferred alkenyl radicals contain 3 to 4 carbon atoms in the chain.

Alkynyl can likewise, in accordance with the number of carbon atoms, be straight-chain or branched and is typically propargyl, but-1-yn-1-yl or but-1-yn-3-yl. The preferred meaning is propargyl.

Halogen and halo substituents will be understood generally as meaning fluoro, chloro, bromo or iodo. Fluoro, chloro or bromo are preferred meanings.

Haloalkyl can contain identical or different halogen atoms, typically fluoromethyl, difluoromethyl, difluorochloromethyl, trifluoromethyl, chloro methyl, dichloromethyl, trichloromethyl, 2,2,2-trifluoroethyl, 2-fluoroethyl, 2-chloroethyl, 2,2,2-trichloroethyl, 3,3,3-trifluoropropyl.

Cycloalkyl is, depending on the ring size, cyclopropyl, cyclobutyl, cyclopentyl, cyclohexyl or cycloheptyl.

A is thienyl, including all 3 isomers.

A special group within the scope is that of the compounds of formula I, wherein
$R_1=C_3-C_6$alkyl, cyclopropyl, cyclobutyl;
$R_2=OR_5$;
$R_3$ and $R_4$ are each independently of the other hydrogen, chloro, bromo, iodo;
$R_5$ $C_2-C_6$alkyl, cyclopropyl or cyclobutyl (subgroup D).

A preferred group within the scope of subgroup D is that of the compounds of the formula I, wherein
A=thienyl[2.3-d],
$R_1=C_3-C_6$alkyl,
$R_2=OR_5$,
$R_3$ and $R_4$ are each independently of the other hydrogen, chloro, bromo, iodo and
$R_5=C_2-C_6$alkyl (subgroup E).

The most preferred compounds of the invention disclosed herein are the following ones:
6-Chloro-2-propoxy-3-propyl-3H-thieno[2.3-d]pyrimidin-4-one (No. 2.41),
6-Chloro-2-propoxy-3-isobutyl-3H-thieno[2.3-d]pyrimidin-4-one (No. 2.42),
6-Chloro-2-isobutoxy-3-propyl-3H-thieno[2.3-d]pyrimidin-4-one (No. 2.83),
6-Chloro-2-propoxy-3-butyl-3H-thieno[2.3-d]pyrimidin-4-one (No. 2.106),
6-Bromo-2-propoxy-3-butyl-3H-thieno[2.3-d]pyrimidin-4-one (No. 2.107),
6-Chloro-2-butoxy-3-propyl-3H-thieno[2.3-d]pyrimidin-4-one (No. 2.112),
6-Bromo-2-butoxy-3-propyl-3H-thieno[2.3-d]pyrimidin-4-one (No. 2.113),
6-Chloro-2-butoxy-3-butyl-3H-thieno[2.3-d]pyrimidin-4-one (No. 2.129),
6-Bromo-2-butoxy-3-butyl-3H-thieno[2.3-d]pyrimidin-4-one (No. 2.130),
6-Chloro-2-butoxy-3-isobutyl-3H-thieno[2.3-d]pyrimidin-4-one (No. 2.131),
6-Bromo-2-butoxy-3-isobutyl-3H-thieno[2.3-d]pyrimidin-4-one (No. 2.132),
6-Bromo-2-propoxy-3-isobutyl-3H-thieno[2.3-d]pyrimidin-4-one (No. 2.133),
6-Chloro-2-ethoxy-3-isobutyl-3H-thieno[2.3-d]pyrimidin-4-one (No. 2.134), 6-Bromo-2-ethoxy-3-isobutyl-3H-thieno[2.3-d]pyrimidin-4-one (No. 2.135),
6-Bromo-2-isobutoxy-3-propyl-3H-thieno[2.3-d]pyrimidin-4-one (No. 2.136).

The compounds of formula I can be prepared as follows thioureaheterocycles IV, in most cases, cyclise immediately (step 3 in scheme 1). In some cases, the cyclysation is carried out in the presence of stronger bases, such as potassium tert-butylate, sodium hydride or potassium hydride in solvents such as tetrahydrofuran, dimethylfoma- Scheme 1

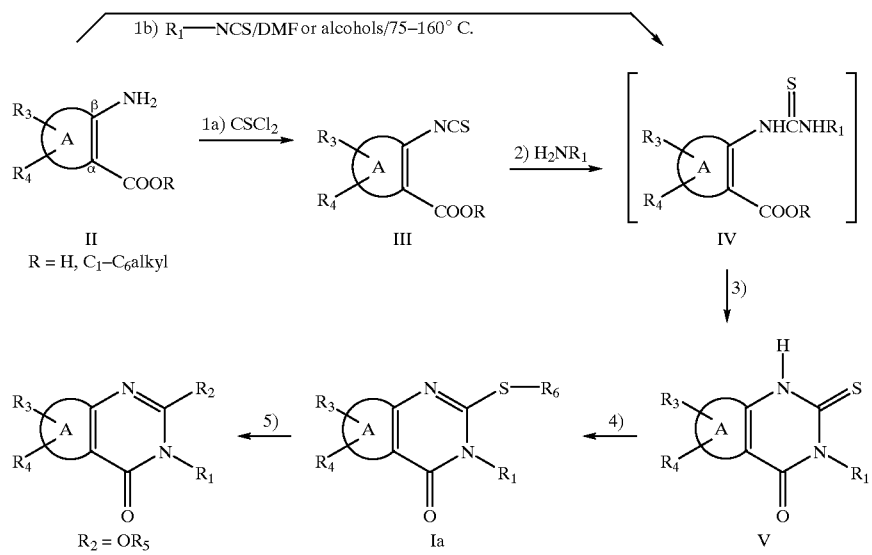

The compounds of formula I are preferably prepared starting from α-amino-β-carboalkoxyheterocycles or α-amino-β-carbocyclic acid heterocycles, some of which, where Het=thienyl, are commercially available (2 isomers). The methyl thiophene-2-amino-3-carboxylate can be prepared, for example, in accordance with Acta Pharm. Suecica 1968, Vol. 5, p.563, according to S. Gronowitz et al. Other heterocycles can be prepared according to instructions in the literature. The synthesis of, for example, ethyl 5-aminothiazole-4-carboxylate and ethyl 5-amino-2-methylthiazole-4-carboxylate is described by Golankiewicz et al. in Tetrahedron 1985, 41, 5989. The reaction of the α-amino-β-carboalkoxyheterocycles or α-amino-β-carbocyclic acid heterocycles with thiophosgene (step 1a in scheme 1) is conveniently carried out in the presence of a base, such as NaOH, KOH, CaCO$_3$, Na$_2$CO$_3$, K$_2$CO$_3$, NaHCO$_3$, N(Et)$_3$, pyridine, and others, in solvents, such as CH$_2$Cl$_2$, CHCl$_3$, ether, tetrahydrofuran and others, possibly in a 2 phase mixture consisting of CHCl$_3$/water or CH$_2$Cl$_2$/water, or toluene/water in the temperature range from 0° C. to reflux temperature. The resulting isothiocyanates are then converted with primary amines, such as n-butylamine, n-propylamine, isopropylamine, allylamine, propargylamine, cyclopropylamine, and others, in a solvent (ether, tetrahydrofuran, CH$_2$Cl$_2$, CHCl$_3$, benzene, toluene, dimethylformamide, dimethylsulfoxide) at 0° C. to reflux temperature into the thioureaheterocycles IV (step 2 in scheme 1), which can also be prepared via reaction of the heterocyclic amines II with isothiocyanatoalkanes such as 1-isothiocyanatopropane, 1-isothiocyanatobutane and others in ethanol, n-propanol, n-butanol, dimethylformamide or dimethylsulfoxide as solvents at temperatures between 50° C. and reflux temperature (step 1b in scheme 1). The mide or dimethylsulfoxide in the temperature range from 20°–140° C. The 2-thioxopyrimidin-4-one derivatives are then deprotonised (using bases such as NaOH, NaH, KH, n-BuLi, Na$_2$CO$_3$, K$_2$CO$_3$ etc.) and are then S-alkylated by the addition of alkylhalides (halo=Br, I) (step 4 in scheme 1). The reaction with methyliodide results in the 2-methylsulfanylpyrimidin-4-one derivative which is an important intermediate for the synthesis of alkoxy-substituted and aminoalkyl-substituted pyrimidin-4-ones. The replacement of the thiomethyl group (step 5 in scheme 1) with alkoxy is most preferably carried out by reaction with metal alkoxides, such as NaOMe, NaOEt, NaO-propyl, in the corresponding alcohol, tetrahydrofurane or dimethylsulfoxide as solvent in the temperature range from 20°–150° C.

The above synthesis route is the first disclosure of how to prepare 3H-thieno[2.3-d]-pyrimidin-4-one derivatives within the structural pattern of formula I herein.

The invention also relates to the intermediates of the formula IV and V, and especially to those wherein A represents thienyl[2.3-d].

The introduction of further substituents into the 5-ring of the thienopyrimidin-4-ones may also conveniently be carried out using metallorganic methodology. Thieno[3.2-d]-pyrimidin-4-ones and thieno[2.3-d]pyrimidin-4-ones, for example, can be deprotonised selectively in 6-position. Particularly suitable bases for this purpose are lithium diisopropylamide (LDA), lithium cyclohexylisopropylamide (LICA), secondary butyl lithium/TMEDA. A great number of the radicals R$_3$ indicated above can be introduced by reacting the resulting anions with electrophilics (step 1 in scheme 2), typically Br$_2$, NBS, F$_2$, ICl, Cl$_2$, F$^+$ reagents.

Scheme 2
Synthesis of special heterocycles

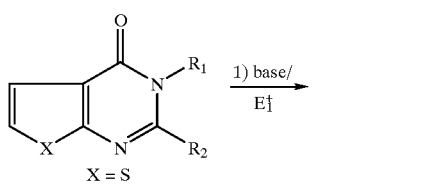

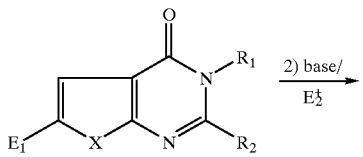

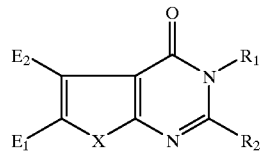

E⁺₁,₂ = NBS (N-Bromsuccinimide), NCS (N-Chlorsuccinimide), Cl₂, Br, FCl, F⁺ reagents.

Scheme 3

Synthesis of Special Thienopyrimidin-4-ones (Special Methods for the Introduction of Halogen into the Thiophene Ring)

a) Thieno[2.3-d]pyrimidin-4-ones:

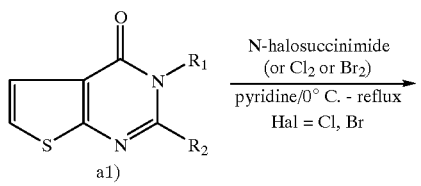

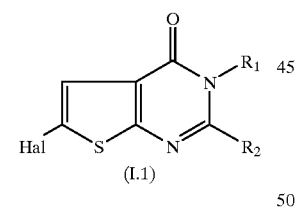

1–3 molar equivalents of N-bromosuccinimide or N-chlorosuccinimide (or Cl₂ gas or Br₂) are used for halogenation. The solvent used is, for example, pyridine in the temperature range from 0° C. to reflux. The reaction time is 1 to 24 hours.

a2) "Pure" Chlorinating Method:

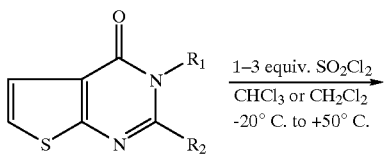

b) Thieno[3.4-d]pyridin-4-ones:

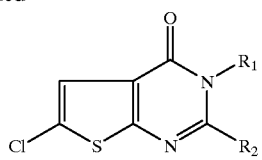

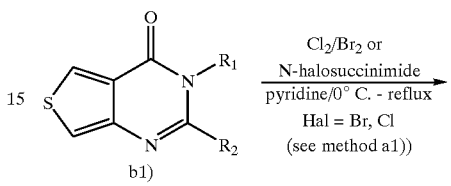

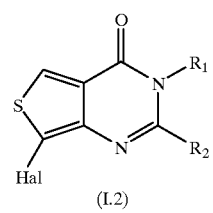

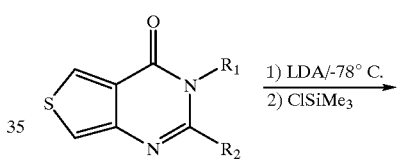

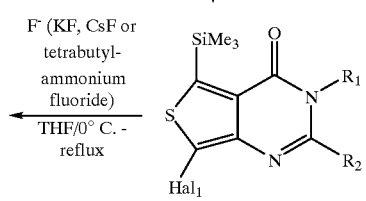

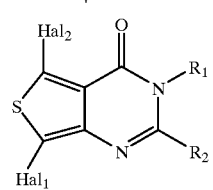

Mixed halogenised compounds (hal₁ different from hal₂) can likewise be prepared in the manner indicated in b2).

Another interesting aspect of this application is the use of metallorganic methodology for the preparation of thieno [3.4-d]pyrimidin-4-ones substituted in 5-position:

Scheme 4

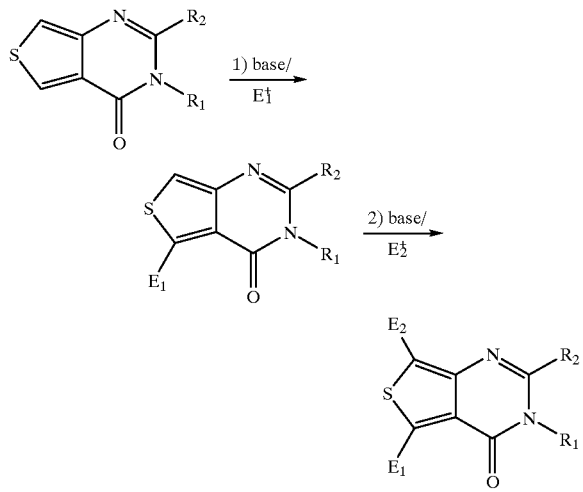

E₁ and E₂ are as defined in scheme 2.

The described reactions are carried out in per se known manner, e.g. in the presence or absence of a suitable solvent or diluent or of a mixture thereof, if appropriate with cooling, at room temperature or with heating, e.g. in the temperature range from about −20° C. to the boiling temperature of the reaction medium, preferably in the range from about −20° C. to about+150° C. and, if required, in a closed vessel, under pressure, in an inert gas atmosphere and/or under anhydrous conditions.

Illustrative examples of such solvents or diluents are: aromatic, aliphatic and alicyclic hydrocarbons and halogenated hydrocarbons, typically benzene, toluene, xylene, chlorobenzene, bromobenzene, petroleum ether, hexane, cyclohexane, dichloromethane, trichloromethane, dichloroethane or trichloroethane; ethers, typically diethyl ether, tert-butylmethyl ether, tetrahydrofuran or dioxane; ketones, typically acetone or methyl ethylketone; alcohols, typically methanol, ethanol, propanol, butanol, ethylene glycol or glycerol; esters, typically ethyl acetate or butyl acetate; amides, typically N,N-dimethylformamide, N,N-dimethylacetamide, N-methylpyrrolidone or hexamethylphosphoric acid triamide; nitriles, typically acetonitrile; and sulfoxides, typically dimethylsulfoxide. Bases used in excess, such as triethylamine, pyridine, N-methylmorpholine or N,N-diethylaniline, can also be used as solvents or diluents.

Suitable bases are, for example, alkali metal hydroxide or alkaline earth metal hydroxide, alkali metal hydride or alkaline earth metal hydride, alkali metal amide or alkaline earth metal amide, alkali metal alkanolate or alkaline earth metal alkanolate, alkali metal carbonate or alkaline earth metal carbonate, alkali metal dialkylamide or alkaline earth metal dialkylamide, or alkali metal alkylsilylamide or alkaline earth metal alkylsilylamide, alkylamines, alkylenediamines, optionally N-alkylated, optionally unsaturated cycloalkylamines, basic heterocycles, ammonium hydroxides and carbocyclic amines. Examples meriting mention are sodium hydroxide, sodium hydride, sodium amide, sodium methanolate, sodium carbonate, potassiumtert-butanolate, potassium carbonate, lithium diisopropylamide, potassium bis(trimethylsilyl)amide, calcium hydride, triethylamine, triethylenediamine, cyclohexylamine, N-cyclohexyl-N,N-dimethylamine, N,N-diethylaniline, pyridine, 4-(N,N-dimethylamino)pyridine, N-methylmorpholine, benzyltrimethylammoniumhydroxide, and 1,8-diazabicyclo [5.4.0]undec-5-ene (DBU).

Quinazolinone derivatives having fungicidal properties are known from WO-94/26722 or EP-A-276825.

Surprisingly, it has now been found that the novel compounds of formula I have, for practical purposes, a very advantageous spectrum of activities for protecting plants against diseases that are caused by fungi as well as by bacteria and viruses.

The compounds of formula I can be used in the agricultural sector and related fields as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g rice), for the protection against fungal infections as well as against phytopatflogenic fungi occurring in the soil.

The compounds I are, for example, effective against the phytopathogenic fungi of the following classes: Fungi imperfecti (e.g. Botrytis, Pyricularia, Helminthosporium, Fusarium, Septoria, Cercospora and Alternaria) and Basidiomycetes (e.g. Rhizoctonia, Hemileia, Puccinia). Additionally, they are also effective against the Ascomycetes classes (e.g. Venturia and Erysiphe, Podosphaera, Monilinia, Uncinula) and of the Oomycetes classes (e.g. Phytophthora, Pythium, Plasmopara). Furthermore, the novel compounds of formula I are effective against phytopathogenic bacteria and viruses (e.g. against Xanthomonas spp, Pseudomonas spp, *Erwinia amylovora* as well as against the tobacco mosaic virus).

Within the scope of this invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinache, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The compounds of formula I are normally used in the form of compositions and can be applied to the crop area or plant to be treated, simultaneously or in succession with further compounds. These further compounds can be e.g. fertilisers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula I can be mixed with other fungicides, resulting in some cases in unexpected synergistic activities.

Mixing components which are particularly preferred are azoles such as propiconazole, difenoconazole, cyproconazole, epoxiconazole, tebuconazole, tetraconazole, fenbuconazole, metconazole, bromuconazole; and also fenpropidine, fenpropimorph, cyprodinile, pyrimethanile, S-methyl benzo-1,2,3-thiadiazole-7-thiocarboxylate; and strobilurines such as azoxystrobine and cresoximemethyl.

Suitable carriers and adjuvants can be solid or liquid and are substances useful in formulation technology, e.g. natural or regenerated mineral substances, solvents, dispersants, wetting agents, tackifiers, thickeners, binders or fertilisers.

A preferred method of applying a compound of formula I, or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

The compounds of formula I are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

The formulation, i.e. the compositions containing the compound of formula I and, if desired, a solid or liquid adjuvant, are prepared in knwon manner, typically by intimately mixing and/or grinding the compound with extenders, e.g. solvents, solid carriers and, optionally, surface active compounds (surfactants).

Suitable solvents may typically be: aromatic hydrocarbons, preferably the fractions containing 8 to 12 carbon atoms such as xylene mixtures or substituted naphthalenes; phthalates such as dibutyl or dioctyl phthalate; aliphatic hydrocarbons such as cyclohexane or paraffins; alcohols and glycols and their ethers and esters such as ethanol, diethylene glycol, 2-methoxyethanol or 2-ethoxyethanol; ketones such as cyclohexanone; strongly polar solvents such as N-methyl-2-pyrrolidone, dimethyl sulfoxide or dimethyl formamide; as well as vegetable oils or epoxidised vegetable oils such as epoxidised coconut oil or soybean oil; and water.

The solid carriers typically used for dusts and dispersible powders are usually natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, including pumice, broken brick, sepiolite or bentonite; and suitable nonsorbent carriers are materials such as calcite or sand. In addition, innumerable pregranulated materials of inorganic or organic origin may be used, typically especially dolomite or pulverised plant residues.

Depending on the compound of formula I to be formulated, suitable surfactants are non-ionic, cationic and/ or anionic surfactants having good emulsifying, dispersing and wetting properties. Surfactants will also be understood to include surfactant mixtures.

Suitable anionic surfactants may be so-called watersoluble soaps as well as water-soluble synthetic surfaceactive compounds.

Illustrative examples of nonionic surfactants are nonylphenol polyethoxyethanols, castor oil polyglycol ether, polyadducts of polypropylene and polyethylene oxide, tributylphenoxy polyethoxyethanol, polyethylene glycol and octylphenoxy polyethoxyethanol. Fatty acid esters of polyoxyethylene sorbitan, such as polyoxyethylene sorbitan trioleate, are also suitable.

The cationic surfactants are preferably quarternary ammonium salts carrying, as N-substituent, at least one $C_8$–$C_{22}$ alkyl radical and, as further substituents, optionally halogenated lower alkyl, benzyl or hydroxy-lower alkyl radicals.

Further surfactants customarily employed in the art of formulation are known to the expert or can be found in the relevant literature.

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

The compositions may also contain further adjuvants such as stabilisers, antifoams, viscosity regulators, binders or tackifiers as well as fertilisers, micronutrient donors or other formulations for obtaining special effects.

The following non-limitative Examples illustrate the above-described invention in more detail. Temperatures are given in degrees Celsius. The following abbreviations are used: Et=ethyl; i-propyl=isopropyl; Me=methyl; m.p.= melting point. "NMR" means nuclear magnetic resonance spectrum. MS=mass spectrum. "%" is percent by weight, unless corresponding concentrations are indicated in other units.

PREPARATION EXAMPLES

Example P-1

3-Propyl-2-thioxo-2,3-dihydro-1H-thieno[3.2-d]pyrimidin-4-one

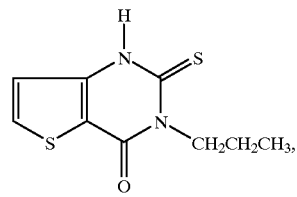

In a sulfonation flask, 1.7 g (0.028 mol) of n-propylamine are added dropwise to 30 ml of tetrahydrofuran and 5.2 g (0.026 mol) of methyl 3-isothiocyanatothiophene-2-carboxylate, dissolved in 30 ml of tetrahydrofuran, such that the internal temperature does not rise above 35° C. The reaction mixture is then stirred for 16 hours at reflux temperature and the tetrahydrofuran is then removed in a water-jet vacuum. The residue is taken up in ethyl acetate and extracted three times with water. The organic phase is then dried over sodium sulfate and the solvent is removed in the water-jet vacuum, giving the 3-propyl-2-thioxo-2,3-dihydro-1 H-thieno[3.2-d]pyrimidin-4-one crude product which can be purified by digestion in tert-butylmethyl ether. The slightly brownish powder (5.3 g) has a melting point of >230° C.

Example P-2
2-Methylsulfanyl-3-propyl-3H-thieno[3.2-d]pyrimidin-4-one

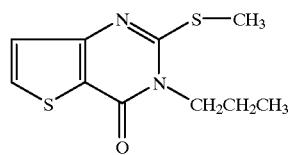

In a sulfonation flask, 0.84 g (0.021 mol) of a ~60% sodium hydride dispersion is added to 20 ml of absolute tetrahydrofuran, and then 4.8 g (0.021 mol) of 3-propyl-2-thioxo-2,3-dihydro-1H-thieno-[3.2-d]pyrimidin-4-one, dissolved in 80 ml of tetrahydrofuran, are added dropwise such that the internal temperature remains constant at about 25° C. The mixture is stirred for 1 hour at room temperature and then 4.3 g (0.03 mol) of methyl iodide are added all at once. The mixture is refluxed for 4 hours and then the tetrahydrofuran is removed in a water-jet vacuum. The residue is taken up in ethyl acetate and the organic phase is extracted three times with water. The organic phase is dried over sodium sulfate and the solvent is removed in the water-jet vacuum, giving the crude product which is purified by column chromatography over silica gel (eluant: ethyl acetate/hexane 1:3). 2-Methylsulfanyl-3-propyl-3H-thieno[3.2-d]pyrimidin-4-one is obtained in virtually quantitative yield and having a melting point of 142–144° C.

Example P-3
6-Bromo-2-methylsulfanyl-3-propyl-3H-thieno[3.2-d]pyrimidin-4-one

[cmpd 1.4]

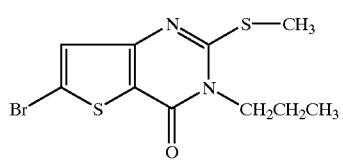

In a sulfonation flask, 9.6 g (0.04 mol) of 2-methylsulfanyl-3-propyl-3H-thieno[3.2-d]-pyrimidin-4-one are added to 200 ml of absolute tetrahydrofuran. Subsequently, 4.07 g (0.042 mol) of lithium diisopropylamide, dissolved in 50 ml of absolute tetrahydrofuran, are added dropwise under $N_2$ such that the internal temperature remains constant at about −78° C. The mixture is stirred for 1 hour at −78° C. and then a solution of 8.5 g (0.048 mol) of N-bromosuccinimide in 40 ml of absolute tetrahydrofuran is added dropwise such that the internal temperature remains constant at about −78° C. The condenser is then removed and the mixture is slowly warmed to room temperature. The tetrahydrofuran is removed in a water-jet vacuum and the residue is dissolved in ethyl acetate. The organic phase is washed with water, dried over sodium sulfate and the ethyl acetate is then removed in the water-jet vacuum. The crude product is purified by column chromatography over silica gel (eluant: ethyl acetate/hexane=1:5), giving 3.8 g of 6-bromo-2-methylsulfanyl-3-propyl-3H-thieno[3.2-d]pyrimidin-4-one in the form of a yellow powder having a melting point of 138–141° C.

Example P-4
2-Propoxy-3-propyl-3H-thieno[3.2-d]pyrimidin-4-one

[cmpd 1.40]

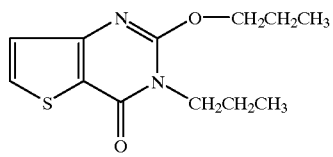

In a sulfonation flask, 1.66 g (0.02 mol) of sodium propylate and 1.5 g (0.00625 mol) of 2-methylsulfanyl-3-propyl-3H-thieno-[3.2-d]pyrimidin-4-one are stirred in 50 ml of absolute n-propanol for 3 hours under $N_2$ at reflux temperature. The n-propanol is then removed in a water-jet vacuum and the residue is taken up in ethyl acetate/water and extracted three times with water. The organic phase is dried over sodium sulfate and the solvent is removed in the water-jet vacuum, giving the crude product which is then purified by column chromatography over silica gel (eluant: ethyl acetate/hexane 1:3). 1.22 g of 2-propoxy-3-propyl-3H-thieno[3.2-d]pyrimidin-4-one are obtained in the form of a beige powder having a melting point of 42–45° C.

Example P-5
7-Chloro-2-propoxy-3-propylthieno[3.4-d]pyrimidin-4-one

[cmpd 3.46]

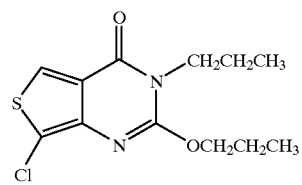

In a sulfonation flask, 2.02 g (0.008 mol) of 2-propoxy-3-propylthieno[3.2-d]pyrimidin-4-one are added, with stirring, to 10 ml of absolute pyridine. The internal temperature is then raised to 70° C. and then 1.60 g (0.012 mol) of N-chlorosuccinimide (NCS) are added over about 5 min in smallish portions. After stirring for 1 hour at 70–75° C., the pyridine is removed in a water-jet vacuum and the residue is taken up in ethyl acetate. The mixture is washed repeatedly with dilute aqueous hydrochloric acid, dried over sodium sulfate and then the solvent is removed in the water-jet vacuum. The crude product so obtained is purified by column chromatography over silica gel (eluant: n-hexane/ethyl acetate=9:1), giving 2.2 g of 7-chloro-2-propoxy-3-propylthieno[3.4-d]pyrimidin-4-one in the form of a green powder having a melting point of 93–95° C.

Example P-6
Methyl 2-isothiocyanatothiophene-3-carboxylate

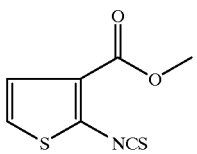

In a sulfonation flask, 50.2 g (0.32 mol) of methyl 2-aminothiophene-3-carboxylate are added to 480 ml of chloroform and 320 ml of water. Then 40.5 g (0.35 mol) of thiophosgene and 1000 ml of saturated aqueous sodium bicarbonate solution are added simultaneously in 40 minutes under stirring. The stirring continued for 1 h at room temperature and then the organic phase is separated. The water phase is extracted twice with chloroform and the organic phase dried over sodium sulfate. After removal of the chloroform in the water-jet vacuum 61.3 g of a dark oil is obtained, which is further purified by column chromatography over silica gel (eluant: ethyl acetate/hexane=1:5). 41.5 g of methyl 2-isothiocyanatothiophene-3-carboxylate are obtained in the form of a brown powder having a melting point of 63–65° C.

Example P-7 (method 1)
Methyl 2-(3-propylthioureido)thiophene-3-carboxylate

[cmpd 9.1]

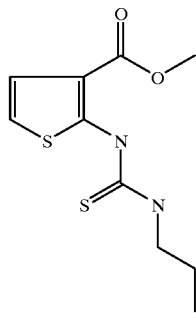

In a sulfonation flask, 13.5 g (0.023 mol) of n-propylamine are added dropwise to 350 ml of tetrahydrofurane and 41.3 g (0.021 mol) of methyl 2-isothiocyanatothiophene-3-carboxylate, such that the internal temperature does not arise above 40° C. The reaction mixture is then stirred for 4 hours at reflux temperature and then the tetrahydrofurane is removed in a water-jet vacuum. The residue is taken up in ethyl acetate and extracted three times with water. The organic phase is then dried over sodium sulfate and the solvent is removed in the water-jet vacuum, giving the crude product, which is purified by column chromatography over silica gel (eluant: ethyl acetate/hexane=1:3). 32.4 g of methyl 2-(3-propylthioureido)-thiophene-3-carboxylate are obtained in the form of a beige powder having a melting point of 123–126° C.

Example P-7 (method 2)
Methyl 2-(3-propylthioureido)thiophene-3-carboxylate

In a sulfonation flask, 2.02 g (0.02 mol) of 1-isothiocynatopropane are added dropwise to 30 ml dimethylformamide and 3.0 g (0.019 mol) of methyl 2-aminothiophene-3-carboxylate. The reaction mixture is then stirred at 130–135° C. for 12 hours and after cooling added to 120 ml of water. The resulting mixture is then extracted three times with ethylacetate and the separated organic phase dried over sodium sulfate. The solvent is then removed in a water-jet vacuum, giving the crude product as a dark oil, which is purified by column chromatography over silica gel (eluant: tert.butylmethylether/hexane=2:3). 2.0 g of methyl 2-(3-propylthioureido)thiophene-3-carboxylate are obtained in the form of a yellow powder having a melting point of 122–124° C.

Example P-8
3-Butyl-2-thioxo-2,3-dihydro-1H-thieno[2.3-d]pyrimidin-4-one

[cmpd 10.4]

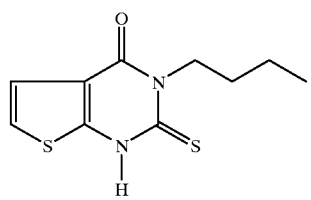

In a sulfonation flask, 0.2 g (0.0049 mol) of a ca. 60% sodium hydride dispersion is added to 20 ml absolute tetrahydrofurane. Then 1.29 g (0.0047 mol) of methyl 2-(3-butylthioureido)thiophene-3-carboxylate, dissolved in 10 ml absolute tetrahydrofurane are added dropwise, such that the internal temperature remains constant at about 25° C. The mixture is stirred at reflux temperature for 3 hours and then the solvent is removed in a water-jet vacuum and the residue taken up in ethylacetate/water. After addition of acetic acid the mixture is extracted three times with ethylacetate and the organic phase dried over sodium sulfate. After removal of the solvent in a water-jet vacuum, 1.06 g of 3-butyl-2-thioxo-2,3-dihydro-1H-thieno[2.3-d]pyrimidin-4-one are obtained in the form of a brown powder having a melting point of 200–203° C.

Example P-9
2-Methylsulfanyl-3-propyl-3H-thieno[2.3-d]pyrimidin-4-one

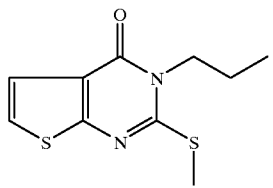

In a sulfonation flask, 2.9 g (0.072 mol) of a ca. 60% sodium hydride dispersion is added to 50 ml of absolute tetrahydrofurane. Then 17.7 g (0.069 mol) of methyl 2-(3-propylthioureido)thiophene-3-carboxylate, dissolved in 100 ml of absolute tetrahydrofurane, are added dropwise, such that the internal temperature remains constant at about 25° C. The mixture is stirred at reflux temperature for 5 hours and after cooling to room temperature 10.9 g (0.077 mol) of methyliodide, dissolved in 10 ml of tetrahydrofurane, are added dropwise. Then the mixture is stirred another 2 hours at reflux temperature. After completion of the reaction, the tetrahydrofurane is removed in the water-jet vacuum and the residue taken up in ethyl acetate. The organic layer is washed twice with water and then dried over sodium sulfate. After removal of the solvent in the water-jet vacuum, the crude product is obtained, which is purified by digestion in n-hexane. 15.1 g of 2-methylsulfanyl-3-propyl-3H-thieno[2.3-d]pyrimidin-4-one are obtained in the form of a slightly yellowish powder having a melting point of 94-96° C.

Example P-10

2-Propoxy-3-propyl-3H-thieno[2.3-d]pyrimidin-4-one

[cmpd 2.40]

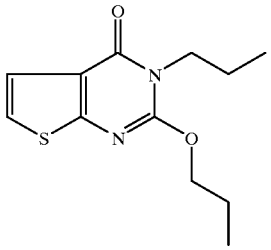

In a sulfonation flask, 12.5 g (0.15 mol) of sodium propylate and 12.0 g (0.05 mol) 2-methylsulfanyl-3-propyl-3H-thieno[2.3-d]pyrimidin-4-one are stirred in 120 ml of absolute n-propanol for 4 hours under nitrogen at reflux temperature. The n-propanol is then removed in a water-jet vacuum and the residue taken up in ethyl acetate/water and the organic phase is extracted twice with water. The organic phase is dried over sodium sulfate and the solvent removed in the water-jet vacuum, giving the crude product, which is then purified by column chromatography over silica gel (eluant: ethyl acetate/hexane=1:3). 6.7 g of 2-propoxy-3-propyl-3H-thieno[2.3-d]pyrimidin-4-one are obtained in the form of a brown resin ($^1$H-NMR-data see table 1 1).

Example P-11

6-Chloro-2-propoxy-3-propyl-3H-thieno[2.3-d]pyrimidin-4-one

[cmpd 2.41]

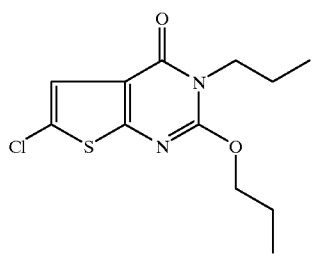

In a sulfonation flask, 10.1 g (0.04 mol) of 2-propoxy-3-propyl-3H-thieno[2.3-d]pyrimidin-4-one are added with stirring to 50 ml of absolute pyridine. The internal temperature is then raised to 70–75° C. and 9.0 g (0.07 mol) of N-chlorosuccinimid (NCS) are added over about 10 minutes in smallish portions. After stirring for 2 hours at 70–75° C., the pyridine is removed in a water-jet vacuum and the residue taken up in ethyl acetate. After washing twice with cold dilute aqueous hydrochloric acid, drying over sodium sulfate and removing the solvent in a water-jet vacuum, the crude product is obtained. The purification of the crude product is accomplished by column chromatography over silica gel (eluant: ethyl acetate/hexane=1:5), giving 7.8 g 6-chloro-2-propoxy-3-propyl-3H-thieno[2.3-d]pyrimidin-4-one in the form of a white powder having a melting point of 62–65° C.

The compounds of the following Table can also be prepared in analogous manner or by another method corresponding to those indicated above:

TABLE 1

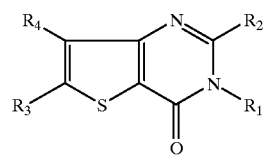

| cmpd No. | $R_2$ | $R_1$ | $R_3$ | $R_4$ | phys. data m.p. ° C. |
|---|---|---|---|---|---|
| 1.1 | SMe | Et | H | H | |
| 1.2 | SMe | n-propyl | H | H | 142–144 |
| 1.3 | SMe | n-propyl | Cl | H | 118–121 |
| 1.4 | SMe | n-propyl | Br | H | 138–141 |
| 1.12 | SMe | i-propyl | H | H | oil, $^1$H-NMR |
| 1.13 | SMe | i-propyl | Cl | H | 91–93 |
| 1.14 | SMe | i-propyl | Br | H | 93–96 |
| 1.19 | OMe | Et | H | H | |
| 1.20 | OMe | n-propyl | H | H | |
| 1.21 | OMe | n-propyl | Cl | H | |
| 1.22 | OMe | n-propyl | Br | H | |
| 1.23 | OMe | n-propyl | SMe | H | |
| 1.28 | OCF$_2$H | n-propyl | H | H | |
| 1.29 | OCF$_2$H | n-propyl | Cl | H | |
| 1.30 | OCF$_2$H | n-propyl | Br | H | |
| 1.31 | OEt | n-propyl | H | H | |
| 1.32 | OEt | n-propyl | Cl | H | |
| 1.33 | OEt | n-propyl | Br | H | |
| 1.37 | OEt | n-propyl | F | H | |
| 1.40 | O-n-propyl | n-propyl | H | H | 42–45 |
| 1.41 | O-n-propyl | n-propyl | Cl | H | 84–86 |
| 1.42 | O-n-propyl | n-propyl | Br | H | 82 |
| 1.50 | O-n-propyl | i-propyl | H | H | oil, $^1$H,NMR |
| 1.51 | O-n-propyl | i-propyl | Cl | H | oil, $^1$H-NMR |
| 1.52 | O-n-propyl | i-propyl | Br | H | oil, $^1$H-NMR |
| 1.58 | O-i-propyl | n-propyl | H | H | |
| 1.59 | O-i-propyl | n-propyl | Cl | H | |
| 1.60 | O-i-propyl | n-propyl | Br | H | |
| 1.61 | O-n-propyl | n-butyl | H | H | |
| 1.62 | O-n-butyl | n-butyl | H | H | |
| 1.63 | O-n-hexyl | n-propyl | H | H | |
| 1.71 | SMe | CH$_2$CH=CH$_2$ | H | H | |
| 1.72 | SMe | CH$_2$CH=CH$_2$ | Cl | H | |
| 1.73 | SMe | CH$_2$CH=CH$_2$ | Br | H | |
| 1.74 | SMe | CH$_2$C≡CH | H | H | |
| 1.75 | SMe | CH$_2$C≡CH | Cl | H | |
| 1.76 | SMe | CH$_2$C≡CH | Br | H | |
| 1.77 | SMe | cyclopropyl | H | H | |
| 1.78 | SMe | cyclopropyl | Cl | H | |
| 1.79 | SMe | cyclopropyl | Br | H | |
| 1.83 | O-n-propyl | n-propyl | I | H | |
| 1.84 | O-n-propyl | CH$_2$CH=CH$_2$ | H | H | |
| 1.85 | O-n-propyl | CH$_2$CH=CH$_2$ | Cl | H | |
| 1.86 | O-n-propyl | CH$_2$CH=CH$_2$ | Br | H | |
| 1.87 | O-n-propyl | CH$_2$C≡CH | H | H | |
| 1.88 | O-n-Propyl | CH$_2$C≡CH | Cl | H | |
| 1.89 | O-n-propyl | CH$_2$C≡CH | Br | H | |
| 1.90 | O-n-propyl | cyclopropyl | H | H | |
| 1.91 | O-n-propyl | cyclopropyl | Cl | Br | |
| 1.92 | O-n-propyl | cyclopropyl | Br | H | |
| 1.96 | O-n-propyl | n-butyl | Cl | H | |
| 1.97 | O-n-butyl | n-butyl | Cl | H | oil |
| 1.98 | O-n-propyl | n-pentyl | H | H | |
| 1.99 | O-n-propyl | n-pentyl | Cl | H | |
| 1.100 | O-n-butyl | n-pentyl | H | H | |
| 1.101 | O-n-butyl | n-pentyl | Br | H | |

TABLE 2

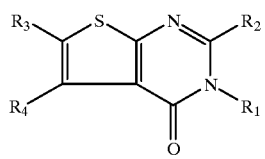

| cmpd No. | R₂ | R₁ | R₃ | R₄ | phys. data m.p. °C. |
|---|---|---|---|---|---|
| 2.1 | SMe | Et | H | H | |
| 2.2 | SMe | n-propyl | H | H | |
| 2.3 | SMe | n-propyl | Cl | H | |
| 2.4 | SMe | n-propyl | Br | H | |
| 2.12 | SMe | i-propyl | H | H | |
| 2.13 | SMe | i-propyl | Cl | H | |
| 2.14 | SMe | i-propyl | Br | H | |
| 2.19 | OMe | Et | H | H | |
| 2.20 | OMe | n-propyl | H | H | oil, ¹H-NMR |
| 2.21 | OMe | n-propyl | Cl | H | 87–89 |
| 2.22 | OMe | n-propyl | Br | H | |
| 2.28 | OCF₂H | n-propyl | H | H | |
| 2.29 | OCF₂H | n-propyl | Cl | H | |
| 2.30 | OCF₂H | n-propyl | Br | H | |
| 2.31 | OEt | n-propyl | H | H | oil, ¹H-NMR |
| 2.32 | OEt | n-propyl | Cl | H | 68–71 |
| 2.33 | OEt | n-propyl | Br | H | 103–107 |
| 2.37 | OEt | n-propyl | F | H | |
| 2.40 | O-n-propyl | n-propyl | H | H | resin, ¹H-NMR |
| 2.41 | O-n-propyl | n-propyl | Cl | H | 62–65 |
| 2.42 | O-n-propyl | i-butyl | Cl | H | oil |
| 2.50 | O-n-propyl | i-propyl | H | H | oil, ¹H-NMR |
| 2.51 | O-n-propyl | i-propyl | Cl | H | 76–78 |
| 2.52 | O-n-propyl | i-propyl | Br | H | |
| 2.58 | O-i-propyl | n-propyl | H | H | |
| 2.59 | O-i-propyl | n-propyl | C | H | |
| 2.60 | O-i-propyl | n-propyl | Br | H | |
| 2.61 | O-n-propyl | n-butyl | H | H | oil, ¹H-NMR |
| 2.62 | O-n-butyl | n-butyl | H | H | oil, ¹H-NMR |
| 2.63 | O-n-hexyl | n-propyl | H | H | |
| 2.71 | SMe | CH₂CH=CH₂ | H | H | |
| 2.72 | SMe | CH₂CH=CH₂ | Cl | H | |
| 2.73 | SMe | CH₂CH=CH₂ | Br | H | |
| 2.74 | SMe | CH₂C≡CH | H | H | |
| 2.75 | SMe | CH₂C≡CH | Cl | H | |
| 2.76 | SMe | CH₂C≡CH | Br | H | |
| 2.77 | SMe | cyclopropyl | H | H | |
| 2.78 | SMe | cyclopropyl | Cl | H | |
| 2.79 | SMe | cyclopropyl | Br | H | |
| 2.83 | O-i-butyl | n-propyl | H | H | |
| 2.84 | O-n-propyl | CH₂CH=CH₂ | H | H | |
| 2.85 | O-n-propyl | CH₂CH=CH₂ | Cl | H | |
| 2.86 | O-n-propyl | CH₂CH=CH₂ | Br | H | |
| 2.87 | O-n-propyl | CH₂C≡CH | H | H | |
| 2.88 | O-n-propyl | CH₂C≡CH | Cl | H | |
| 2.89 | O-n-propyl | CH₂C≡CH | Br | H | |
| 2.90 | O-n-propyl | cyclopropyl | H | H | 73–75 |
| 2.91 | O-n-propyl | cyclopropyl | Cl | Br | |
| 2.92 | O-n-propyl | cyclopropyl | Br | H | 128–130 |
| 2.96 | OMe | n-propyl | F | H | |
| 2.97 | OMe | n-butyl | H | H | |
| 2.98 | OMe | n-butyl | Cl | H | |
| 2.99 | OMe | i-propyl | H | H | oil |
| 2.100 | OEt | n-propyl | I | H | |
| 2.101 | OEt | n-butyl | H | H | oil, ¹H-NMR |
| 2.102 | OEt | n-butyl | Cl | H | oil, ¹H-NMR |
| 2.103 | OEt | n-pentyl | H | H | |
| 2.104 | OEt | n-pentyl | Br | H | |

TABLE 2-continued

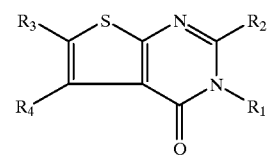

| cmpd No. | R₂ | R₁ | R₃ | R₄ | phys. data m.p. °C. |
|---|---|---|---|---|---|
| 2.105 | O-n-propyl | n-propyl | I | H | 93–95 |
| 2.106 | O-n-propyl | n-butyl | Cl | H | 82–84 |
| 2.107 | O-n-propyl | n-butyl | Br | H | 68–70 |
| 2.108 | O-n-propyl | n-butyl | I | H | 80–82 |
| 2.111 | O-n-butyl | n-propyl | H | H | oil, ¹H-NMR |
| 2.112 | O-n-butyl | n-propyl | Cl | H | 49–51 |
| 2.113 | O-n-butyl | n-propyl | Br | H | 59–64 |
| 2.118 | SMe | n-butyl | H | H | oil, ¹H-NMR |
| 2.129 | O-n-butyl | n-butyl | Cl | H | oil |
| 2.130 | O-n-butyl | n-butyl | Br | H | oil |
| 2.131 | O-n-butyl | i-butyl | Cl | H | |
| 2.132 | O-n-butyl | i-butyl | Br | H | |
| 2.133 | O-n-propyl | i-butyl | Br | H | |
| 2.134 | O-ethyl | i-butyl | Cl | H | |
| 2.135 | O-ethyl | i-butyl | Br | H | |
| 2.136 | O-i-butyl | n-propyl | Br | H | |
| 2.137 | O-n-propyl | i-butyl | Cl | H | oil |
| 2.138 | O-n-propyl | i-butyl | Br | H | oil |

TABLE 3

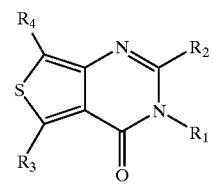

| cmpd No. | R₂ | R₁ | R₃ | R₄ | phys. data m.p. °C. |
|---|---|---|---|---|---|
| 3.1 | SMe | Et | H | H | |
| 3.2 | SMe | n-propyl | H | H | 130–133 |
| 3.3 | SMe | i-propyl | H | H | |
| 3.4 | SMe | n-butyl | H | H | |
| 3.5 | SMe | n-propyl | Cl | Cl | |
| 3.6 | SMe | n-propyl | Br | Br | |
| 3.7 | OMe | n-propyl | H | H | |
| 3.8 | OMe | n-propyl | Cl | Cl | |
| 3.9 | OMe | n-propyl | Br | Br | |
| 3.10 | OEt | n-propyl | H | H | |
| 3.11 | OEt | n-propyl | Cl | Cl | |
| 3.12 | O-n-propyl | n-propyl | H | H | oil, ¹H-NMR |
| 3.13 | O-n-propyl | i-propyl | H | H | |
| 3.14 | O-n-propyl | n-propyl | Cl | Cl | |
| 3.15 | O-n-propyl | n-propyl | Br | Br | 90–93 |
| 3.16 | O-n-propyl | i-propyl | Cl | Cl | oil |
| 3.17 | O-n-propyl | n-propyl | F | F | |
| 3.18 | O-n-propyl | n-butyl | H | H | |
| 3.19 | O-i-propyl | n-propyl | H | H | |
| 3.20 | O-i-propyl | n-propyl | Cl | Cl | |
| 3.21 | O-i-propyl | n-propyl | Br | Br | |
| 3.22 | O-n-butyl | n-propyl | H | H | |
| 3.23 | O-n-butyl | i-propyl | H | H | |
| 3.26 | SMe | Cl | Cl | H | |
| 3.27 | SMe | Br | Br | H | |
| 3.28 | SMe | CH₂CH=CH₂ | H | H | |

TABLE 3-continued

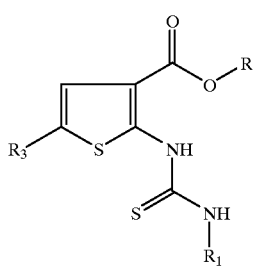

| cmpd No. | R$_2$ | R$_1$ | R$_3$ | R$_4$ | phys. data m.p. ° C. |
|---|---|---|---|---|---|
| 3.29 | SMe | CH$_2$CH=CH$_2$ | Br | H | |
| 3.30 | SMe | CH$_2$C≡CH | H | H | |
| 3.31 | SMe | CH$_2$C≡CH | Br | H | |
| 3.32 | SMe | H | H | H | |
| 3.33 | SMe | Cl | Cl | H | |
| 3.36 | O-n-propyl | n-propyl | Cl | H | |
| 3.37 | O-n-propyl | n-propyl | Br | H | |
| 3.38 | O-n-propyl | CH$_2$CH=CH$_2$ | H | H | |
| 3.39 | O-n-propyl | CH$_2$CH=CH$_2$ | Br | H | |
| 3.40 | O-n-propyl | CH$_2$C≡CH | H | H | |
| 3.41 | O-n-propyl | CH$_2$C≡CH | Br | H | |
| 3.42 | O-n-propyl | cyclopropyl | H | H | |
| 3.43 | O-n-propyl | cyclopropyl | Cl | H | |
| 3.46 | O-n-propyl | n-propyl | H | Cl | 93–95 |
| 3.47 | O-n-propyl | n-propyl | H | Br | 91–93 |
| 3.51 | O-n-butyl | n-propyl | H | H | 70–71 |
| 3.52 | O-n-butyl | n-propyl | H | Br | |
| 3.53 | O-n-butyl | n-butyl | H | H | |
| 3.54 | O-n-butyl | n-butyl | H | Cl | |

TABLE 9

IV'

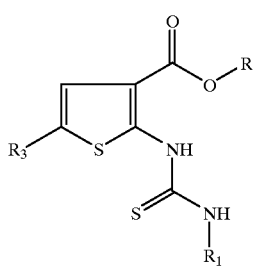

| cmpd No. | R | R$_1$ | R$_3$ | phys. data m.p. ° C. |
|---|---|---|---|---|
| 9.1 | Me | n-propyl | H | 123–126 |
| 9.2 | Et | n-propyl | H | |
| 9.3 | n-propyl | n-propyl | H | |
| 9.4 | Me | n-propyl | Cl | |
| 9.5 | Me | n-propyl | Br | |
| 9.6 | Me | n-butyl | H | 109–111 |
| 9.7 | Et | n-butyl | H | |
| 9.8 | Me | n-butyl | Cl | |
| 9.9 | Me | n-butyl | Br | |
| 9.10 | Me | n-pentyl | H | 80–82 |
| 9.11 | Me | n-hexyl | H | |

TABLE 10

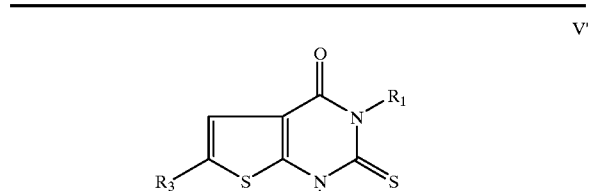

V'

| cmpd No. | R$_1$ | R$_3$ | phys. Data m.p. ° C. |
|---|---|---|---|
| 10.1 | n-propyl | H | 224–228 |
| 10.2 | n-propyl | Cl | |
| 10.3 | n-propyl | Br | |
| 10.4 | n-butyl | H | 200–203 |
| 10.5 | n-butyl | Cl | |
| 10.6 | n-butyl | Br | |
| 10.7 | n-pentyl | H | 195–198 |
| 10.8 | n-hexyl | H | |

TABLE 11

| Ex. No. | $^1$H-NMR data (ppm/multiplicity/number of protons); solvent CDCl$_3$ |
|---|---|
| 1.12 | 1.47/d/6H; 4.06/s/3H; 5.48/m/1H; 6.96/d/1H; 7.34/d/1H |
| 1.51 | 1.08/t/3H; 1.48/d/6H; 1.86/m/2H; 4.38/m/2H; 5.48/m/1 H; 6.94/s/1 H |
| 1.52 | 1.07/t/3H; 1.48/d/6H; 1.86/m/2H; 4.48/m/2H; 5.49/m/1 H; 7.09/s/1 H |
| 2.20 | 0.97/t/3H; 1.69/m/2H; 4.03/t/2H; 4.07/s/3H; 6.98/d/1 H; 7.36/d/1 H |
| 2.31 | 0.96/t/3H; 1.47/t/3H; 1.69/m/2H; 4.04/t/2H;4.50/q/2H; 6.95/d/1H; 7.34/d/1H |
| 2.40 | 0.97/t/3H; 1.06/t/3H; 1.70/m/2H; 1.85/m/2H; 4,04/t/2H; 4.40/t/2H; 6.96/d/1H; 7.34/d/1H |
| 2.61 | 0.96/t/3H; 1.07/t/3H; 1.39/m/2H; 1.70/m/2H; 1 ;85/m/2H; 4.10/t/2H; 4.39/t/3H; 7.12/d/1H; 7.68/d/1H |
| 2.62 | 0.93-1.03/2xt/6H; 1.37-1 ;83/m/8H; 4.07/t/2H; 4.44/t/2H; 6.95/d/1 H; 7.33/d/1 H |
| 2.99 | 1.47/d/6H; 4.07/s/3H; 5.48/s/1H; 6.95/d/1H; 7.34/d/1H |
| 2.101 | 0.96/t/3H; 1.34-1.45/m/SH; 1.65/m/2H; 4.07/t/2H; 4.48/q/2H; 6.95/d/1 H; 7.34/dIlH |
| 2.102 | 0.95/t/3H; 1.33-1.43/m/SH; 1.63/m/2H; 4.05/t/2H; 4.47/q/2H; 7.16/s/1 H |
| 2.111 | 0.93-1.03/2xt/6H; 1.44-1.83/m/6H; 4.04/t/2H; 4.44/t/2H; 6.95/d/1 H; 7.34/d/1 H |
| 2.118 | 0.98/t/3H; 1.41/m/2H; 1.75/m/2H; 2.62/s/2H; 4.12/t/2H; 7.05/d/1H; 7.38/d/1H |
| 3.12 | 0.96/t/3H; 1.05/t/3H; 1.68/q/2H; 1.83/q/2H; 3.99/t/2H; 4.36/t/3H; 7.15/d/1H; 8.17/d/1H |

Formulation Examples for Compounds of Formula I

Example F-1.1 to F-1.3
Emulsifiable Concentrates

| Components | F-1.1 | F-1.2 | F-1.3 |
|---|---|---|---|
| compound of Tables 1 to 3 | 25% | 40% | 50% |
| calcium dodecylbenzenesulfonate | 5% | 8% | 6% |
| castor oil polyethylene glycol ether (36 mol ethylenoxy units) | 5% | — | — |
| tributylphenolpolyethylene glycol ether (30 mol ethylenoxy units) | — | 12% | 4% |
| cyclohexanone | — | 15% | 20% |
| xylene mixture | 65% | 25% | 20% |

Emulsions of any desired concentration can be prepared by diluting such concentrates with water.

Example F-2

Emulsifiable Concentrate

| Components | F-2 |
| --- | --- |
| compound of Tables 1 to 3 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
| --- | --- | --- | --- | --- |
| compound of Tables 1 to 3 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160–190°) | — | — | 94% | — |

The solutions are suitable for use in the form of microdrops.

Examples F-4.1 to F-4.4

Granulates

| Components | F-4.1 | F-4.2 | F-4.3 | F-4.4 |
| --- | --- | --- | --- | --- |
| compound of Tables 1 to 3 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
| --- | --- | --- |
| compound of Tables 1 to 3 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
| --- | --- | --- | --- |
| compound of Tables 1 to 3 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Biological Examples

Fungicidal Actions

B-1: Action Against *Puccinia graminis* on Wheat a) Residual-protective action 6 days after sowing, wheat plants are sprayed to drip point with an aqueous spray mixture (0.02% active ingredient) prepared from a wettable powder formulation of the test compound and infected 24 hours later with a uredo spore suspension of the fungus. After an incubation time of 48 hours (conditions: 95 to 100% relative humidity at 20° C.), the plants are stood at 22° C. in a greenhouse. Evaluation of fungal infestation is made 12 days after infection.

b) Systemic action

Wheat plants are drenched 5 days after sowing with an aqueous spray mixture (0.006% a.i., based on the volume of the soil) prepared from a wettable powder formulation of the test compound. Care is taken that the spray mixture does not come into contact with the growing parts of the plants. After 48 hours, the plants are infected with a uredospore suspension of the fungus. After an incubation period of 48 hours (conditions: 95 to 100% relative humidity at 20° C.), the plants are stood at 22° C. in a greenhouse. Evaluation of the fugal infestation is made 12 days after infection.

Compounds of Tables 1–3 show good activity.

Example B-2

Action Against *Colletotrichum lagenarium* on Cucumbers

After a growth period of 2 weeks, cucumber plants are sprayed with an aqueous spray mixture (concentration 0.002%) prepared from a wettable powder formulation of the test compound and infected 2 days later with a spore suspension ($1.5 \times 10^5$ spores/ml) of the fungus and incubated for 36 hours at 23° C. and high humidity. Incubation is then continued at normal humidity and c. 22° C. Evaluation of the fungal infestation is made 8 days after infection.

The compounds of the Tables 1–3 show good activity.

Example B-3

Residual-protective Action Against *Venturia inaeaualis* on Apples

Apple cuttings with fresh shoots 10 to 20 cm long are sprayed to drip point with a spray mixture (0.02% a.i.) prepared from a wettable powder formulation of the test compound. The plants are infected 24 hours later with a conidia suspensionn of the fungus. The plants are then incubated for 5 days at 90 to 100% relative humidity and stood in a greenhouse for a further 10 days at 20 to 24° C. Evaluation of the fungal infestation is made 12 days after infection.

Compounds of Tables 1–3 show good activity.

Example B-4
Action Against *Erysiphe graminis* on Barley
a) Residual-protective Action Barley plants about 8 cm in height are sprayed to drip point with a spray mixture (0.02% a.i.) prepared from a wettable powder formulation of the test compound, and the treated plants are dusted with conidia of the fungus 3 to 4 hours later. The infected plants are stood in a greenhouse at 22° C. Evaluation of the fungal infection is made 12 days after infection.

b) Systemic Action

Barley plants about 8 cm in height are drenched with an aqueous spray mixture (0.002% a.i., based on the volume of the soil) prepared from a wettable powder formulation of the test compound. Care is taken that the spray mixture does not come into contact with the growing parts of the plants. The treated plants are dusted 48 hours later with conidia of the fugus. The infected plants are then stood in a greenhouse at 22° C. Evaluation of the fungal infestation is made 12 days after infection.

Compared with the control plants, infestation of the plants treated with compounds of formula I, for example the compounds 1.40, 1.41, 1.42, 1.50, 1.51, 1.52, 1.97, 2.20, 2.21, 2.31, 2.32, 2.33, 2.40, 2.41, 2.42, 2.50, 2.51, 2.61, 2.62, 2.83, 2.90, 2.92, 2.99, 2.101, 2.102, 2.105, 2.106, 2.107, 2.108, 2.111, 2.112, 2.113, 2.129, 2.130, 2.131, 2.132, 2.133, 2.134, 2.135, 2.136, 3.12, 3.15, 3.16, 3.46, 3.47 and 3.51, is 20% or less. The following compounds exhibit superior activities (no infestation at all): 2.41, 2.42, 2.83, 2.106, 2.107, 2.112, 2.113, 2.129, 2.130, 2.131, 2.132, 2.133, 2.134, 2.135, 2.136.

Example B-5
Action Against *Podosrhaera leucotricha* on Apple Shoots

Apple cuttings with fresh shoots about 15 cm long are sprayed with a spray mixture (0.06% a.i.). The plants are infected 24 hours later with a conidia suspension of the fungus and stood in a climatic chamber at 70% relative humidity and 20° C. Evaluation of the fugal infestation is made 12 days after infection.

Compounds of Tables 1–3 show good activity. The following compounds exhibit especially strong efficacy: 2.41, 2.42, 2.83, 2.106, 2.107, 2.112, 2.113, 2.129, 2.130, 2.131, 2.132, 2.133, 2.134, 2.135, 2.136 (0–5% infestation).

Example B-6
Action Against *Plasmopara viticola* on Vines
a) Residual-preventive Action:

Vine cuttings of the Chasselas variety are raised in a greenhouse. At the 10-leaf stage, 3 plants are sprayed with a spray mixture (200 ppm a.i.). After the spray coating has dried, the plants are infected uniformly on the underside of the leaves with a spore suspension of the fungus. The plants are then kept in a humidity chamber for 8 days, after which time marked symptoms of disease are observed on the control plants. The number and size of the infected areas on the untreated plants act as an indicator of the efficacy of the tested compounds.

b) Curative Action:

Vine cuttings of the Chasselas variety are raised in a greenhouse and sprayed at the 10-leaf stage on the underside of the leaves with a spore suspension of Plasmopara viticola. After 24 hours in the humidity chamber, the plants are sprayed with a spray mixture (200 ppm a.i.). The plants are then kept for another 7 days in the humidity chamber. After this time the control plants exhibit symptoms of the disease. The number and size of the infected areas on the untreated plants act as an indicator of the efficacy of the tested compounds.

Compoundas of Tables 1–3 show good efficacy.

Example B-7
Action Against *Uncinula necator* on Vines 5 week old vine cuttings are sprayed with a spray mixture (200 ppm a.i.) prepared from a wettable powder formulation of the test compound. The plants are infected 24 hours later by conidias from strongly infested vine leafs that are shaken off over the test plants. The plants are then incubated at 26° C. and 60% relative humidity. The evaluation of the fungal infestation is made ca. 14 days after infection.

Compared with the control plants, infestation of the plants treated with compounds of formula 1, for example the compounds 1.40, 1.41, 1.42, 1.50, 1.51, 1.52, 1.97, 2.20, 2.21, 2.31, 2.32, 2.33, 2.40, 2.41, 2.42, 2.44, 2.50, 2.51, 2.61, 2.62, 2.83, 2.90, 2.92, 2.99, 2.101, 2.102, 2.105, 2.106, 2.107, 2.108, 2.111, 2.112, 2.113, 2.129, 2.130, 2.131, 2.132, 2.133, 2.134, 2.135, 2.136, 3.12, 3.15, 3.16, 3.46, 3.47 and 3.51, is 20% or less. The following compounds exhibit superior activities (no infestation at all): 2.41, 2.42, 2.83, 2.106, 2.107, 2.112, 2.113, 2.129, 2.130, 2.131, 2.132, 2.133, 2.134, 2.135, 2.136.

What is claimed is:

1. A compound of the formula

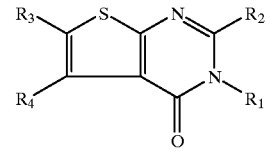

wherein
$R_1$ is n-propyl;
$R_2$ is O-n-propyl;
$R_3$ is chloro; and
$R_4$ is hydrogen.

2. A composition for controlling or preventing phytopathogenic pests comprising an effective pest controlling or preventing amount of a compound according to claim 1 and a suitable carrier.

3. A method of controlling or preventing infestation of cultivated plants by phytopathogenic microorganisms by application of an effective microorganism controlling or preventing amount of a compound according to claim 1 to seeds, to plants, to parts thereof or to the locus thereof.

* * * * *